US011000224B2

(12) United States Patent
Lee et al.

(10) Patent No.: US 11,000,224 B2
(45) Date of Patent: May 11, 2021

(54) METHOD AND APPARATUS OF MONITORING ANAESTHESIA AND CONSCIOUSNESS DEPTH THROUGH BRAIN NETWORK ANALYSIS

(71) Applicant: KOREA UNIVERSITY RESEARCH AND BUSINESS FOUNDATION, Seoul (KR)

(72) Inventors: Seong-Whan Lee, Seoul (KR); Minji Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 330 days.

(21) Appl. No.: 16/118,566

(22) Filed: Aug. 31, 2018

(65) Prior Publication Data

US 2019/0069841 A1    Mar. 7, 2019

(30) Foreign Application Priority Data

Sep. 5, 2017   (KR) .......................... 10-2017-0113260
Jul. 2, 2018   (KR) .......................... 10-2018-0076459

(51) Int. Cl.
*A61B 5/00*     (2006.01)
*A61B 5/316*    (2021.01)
*A61B 5/374*    (2021.01)

(52) U.S. Cl.
CPC ............ *A61B 5/4821* (2013.01); *A61B 5/316* (2021.01); *A61B 5/374* (2021.01); *A61B 5/7203* (2013.01)

(58) Field of Classification Search
CPC ... A61B 5/4821; A61B 5/048; A61B 5/04012; A61B 5/7203
See application file for complete search history.

(56) References Cited

U.S. PATENT DOCUMENTS

2014/0316217 A1*  10/2014  Purdon ................ A61B 5/4821
                                                    600/301
2016/0042514 A1*  2/2016  Amat Roldan ...... A61B 8/0891
                                                    382/131
2017/0001016 A1*  1/2017  De Ridder ......... A61N 1/36135

FOREIGN PATENT DOCUMENTS

| JP | 2016-520375 A    | 7/2016  |
| KR | 10-1079785 B1    | 11/2011 |
| KR | 10-2012-0000371 A | 1/2012  |
| KR | 10-1111498 B1    | 2/2012  |

(Continued)

OTHER PUBLICATIONS

Lee, Minji, et al. "Network Properties in Transitions of Consciousness During Propofol-Induced Sedation", *Scientific Reports*, Dec. 1, 2017, vol. 7, pp. 1-13 (13 pages in English).

*Primary Examiner* — Devin B Henson
*Assistant Examiner* — Joseph A Tombers
(74) *Attorney, Agent, or Firm* — NSIP Law (57) ABSTRACT

A method of monitoring an anesthesia and consciousness depth through brain network analysis by a computing device according to the present disclosure includes: acquiring a user's brain signals extracted during anesthesia; performing pre-treatment to the acquired brain signals to be suitable for brain network analysis; calculating a functional connectivity value between two channels for each frequency based on the pre-treated brain signals and performing brain network analysis; determining an anesthesia and consciousness depth of the user based on features of the analyzed brain network; and providing the determined anesthesia and consciousness depth of the user through a user interface.

8 Claims, 5 Drawing Sheets

(56) References Cited

FOREIGN PATENT DOCUMENTS

| KR | 10-1248118 B1 | 3/2013 |
|---|---|---|
| KR | 10-2013-0093414 A | 8/2013 |
| KR | 10-1395197 B1 | 5/2014 |
| KR | 10-1400362 B1 | 5/2014 |
| KR | 10-1653910 B1 | 9/2016 |

\* cited by examiner

METHOD AND APPARATUS OF MONITORING ANAESTHESIA AND CONSCIOUSNESS DEPTH THROUGH BRAIN NETWORK ANALYSIS

CROSS-REFERENCE TO RELATED APPLICATION

This application claims the benefit under 35 USC 119(a) of Korean Patent Application Nos. 10-2017-0113260 and 10-2018-0076459 filed on Sep. 5, 2017 and Jul. 2, 2018 in the Korean Intellectual Property Office, the entire disclosures of which are incorporated herein by reference for all purposes.

TECHNICAL FIELD

The present disclosure relates to a method and apparatus of monitoring an anesthesia and consciousness depth through brain network analysis.

BACKGROUND

In general, during a medical practice such as surgery and treatment, it is vital to properly maintain the depth of anesthesia and consciousness. If anesthetized lightly, a patient may awaken during surgery and suffer pain, whereas if anesthetized deeply, the patient may die of complications from heart attack. A bigger problem is that when the patient under anesthesia has difficulty in breathing during surgery, he/she cannot express him/herself. Such accidents caused by anesthesia can happen to anyone by surprise and immediately lead to the patient's death. Therefore, the best measure is prevention. In order to prevent such accidents, the depth of anesthesia and consciousness needs to be quantitatively measured. However, at present, the depth of anesthesia is determined by experience and knowledge of an anesthesiologist who understands the status of a patient and regulates the dose of anesthetic. Accordingly, an apparatus capable of objectively measuring the depth of anesthesia is needed.

A Bispectral index (BIS) or entropy index as a representative technology used to monitor a patient currently accounts for 90% or more of the anesthesia depth monitoring market and assesses the depth of anesthesia based on brain activity. Particularly, the BIS values range from 1 to 100 to indicate the depth of anesthesia, and values between 40 and 60 are known as suitable for surgery. Values lower than 40 indicate that a patient is anesthetized too deeply and values higher than 60 indicates that the patient is anesthetized lightly. When a value is equal to or higher than 80, there is a high likelihood of anesthesia accidents such as "anesthesia awareness" in which the patient can feel external stimulus and which can cause the patient to recall pain. The anesthesia awareness during surgery means that the patient awakens under anesthesia and feels pain during surgery but cannot move. If the patient feels pain and paralysis, the patient is very highly likely to suffer "post-traumatic stress disorder" including fear of death, anxiety, etc. That is, in the current anesthesia depth monitoring technologies, it is desirable to maintain anesthesia within a proper BIS range. In this case, the patient can quickly recover from anesthesia after surgery and does not suffer from vomiting or dizziness.

However, these technologies are just used as reference to determine the depth of anesthesia and consciousness. The final determination of consciousness or unconsciousness requires the subjective judgement of a doctor and is often different from the result of sedation rating scales. Also, these technologies take time up to 60 seconds to quantify the result and thus cannot immediately handle medical accidents which may can happen unexpectedly. Further, these technologies are highly reliable in general anesthesia but have low reliability and performance in classification of sedation anesthesia state classification and thus actually have limitations in consciousness depth monitoring. Accordingly, there is a need for an anesthesia and consciousness depth monitoring system capable of considering various environmental variables and helping doctors properly regulate the dose of anesthetic and minimize the occurrence of medical accidents.

As a conventional technology of measuring an anesthesia and consciousness depth using bio-signals, Korean Patent No. 10-1079785 (entitled "EEG analyzer for index calculation of depth anesthesia) discloses a technology of extracting multiple parameters and extracting a proper parameter for each environment or user based on the correlation between anesthesia depths. However, this technology relates to extraction of features rather than development of single index and thus is not suitable to find out an anesthesia and consciousness depth changing according to various environmental variables. Further, Korean Patent No. 10-1111498 (entitled "Depth of anesthesia monitoring system and method using bio-signal analysis and learning process) analyzes various bi-signals including electroencephalogram, electrocardiogram, and blood pressure. However, as the number of bio-signals used increases, it becomes difficult to apply this technology in real clinic practice due to physical complexity and cost.

However, the above-described technologies suggest different types of anesthesia and consciousness depth indexes, respectively, but cannot accurately distinguish consciousness and unconsciousness.

SUMMARY

In view of the foregoing, the present disclosure provides a method and apparatus of monitoring an anesthesia and consciousness depth capable of accurately telling the moment of transition between consciousness and unconsciousness and thus improving the accuracy in determination of consciousness and unconsciousness and minimizing physical and psychological damage caused by anesthesia.

According to a first aspect of the present disclosure, a method of monitoring an anesthesia and consciousness depth through brain network analysis by a computing device includes: acquiring a user's brain signals extracted during anesthesia; performing pre-treatment to the acquired brain signals to be suitable for brain network analysis; calculating a functional connectivity value between two channels for each frequency based on the pre-treated brain signals and performing brain network analysis; determining an anesthesia and consciousness depth of the user based on features of the analyzed brain network; and providing the determined anesthesia and consciousness depth of the user through a user interface.

According to a second aspect of the present disclosure, an apparatus of monitoring an anesthesia and consciousness depth through brain network analysis includes: a memory in which a program configured to perform a method of monitoring an anesthesia and consciousness depth through brain network analysis is stored; and a processor that executes the program. Upon execution of the program, the processor acquires a user's brain signals extracted during anesthesia, performs pre-treatment to the acquired brain signals to be suitable for brain network analysis, calculates a functional connectivity value between two channels for each frequency based on the pre-treated brain signals and performs brain network analysis, determines an anesthesia and consciousness depth of the user based on features of the analyzed brain network, and provides the determined anesthesia and consciousness depth of the user through a user interface.

According to the present disclosure, an anesthesia and consciousness depth can be determined based on a variation in brain network state when an anesthetic is administered, on the basis of a brain network state of a patient before anesthesia. Since brain signals measured from the patient in a waking state are used as a criterion to determine an anesthesia and consciousness depth. Therefore, it is possible to solve the problem of different criteria of index for each person and thus possible to improve the reliability of the system.

Particularly, it is possible to accurately find out the moment of transition between consciousness and unconsciousness and thus possible to accurately measure consciousness depth. The present disclosure is practical in that consciousness depth can be measured with signals from the occipital lobe.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "unit" includes a unit implemented by hardware, a unit implemented by software, and a unit implemented by both of them. One unit may be implemented by two or more pieces of hardware, and two or more units may be implemented by one piece of hardware. However, the "unit" is not limited to the software or the hardware and may be stored in an addressable storage medium or may be configured to implement one or more processors. Accordingly, the "unit" may include, for example, software, object-oriented software, classes, tasks, processes, functions, attributes, procedures, sub-routines, segments of program codes, drivers, firmware, micro codes, circuits, data, database, data structures, tables, arrays, variables and the like. The components and functions provided in the "units" can be combined with each other or can be divided up into additional components or "units". Further, the components and the "units" may be configured to implement one or more CPUs in a device or a secure multimedia card.

An "anesthesia and consciousness depth monitoring apparatus" described herein may be implemented with computers or portable devices which can access a server or another device through a network. Herein, the computers may include, for example, a notebook, a desktop, and a laptop equipped with a WEB browser. For example, the portable devices are wireless communication devices that ensure portability and mobility and may include all kinds of hand-held-based wireless communication devices such as IMT (International Mobile Telecommunication)-2000, CDMA (Code Division Multiple Access)-2000, W-CDMA (W-Code Division Multiple Access), Wibro (Wireless Broadband Internet), LTE (Long Term Evolution)-based devices, smart-phones, tablet PCs, and the like. Further, the "network" may be implemented as wired networks such as a Local Area Network (LAN), a Wide Area Network (WAN) or a Value Added Network (VAN) or all kinds of wireless networks such as a mobile radio communication network or a satellite communication network.

Hereinafter, an embodiment of the present disclosure will be described in detail.

Figure 1:
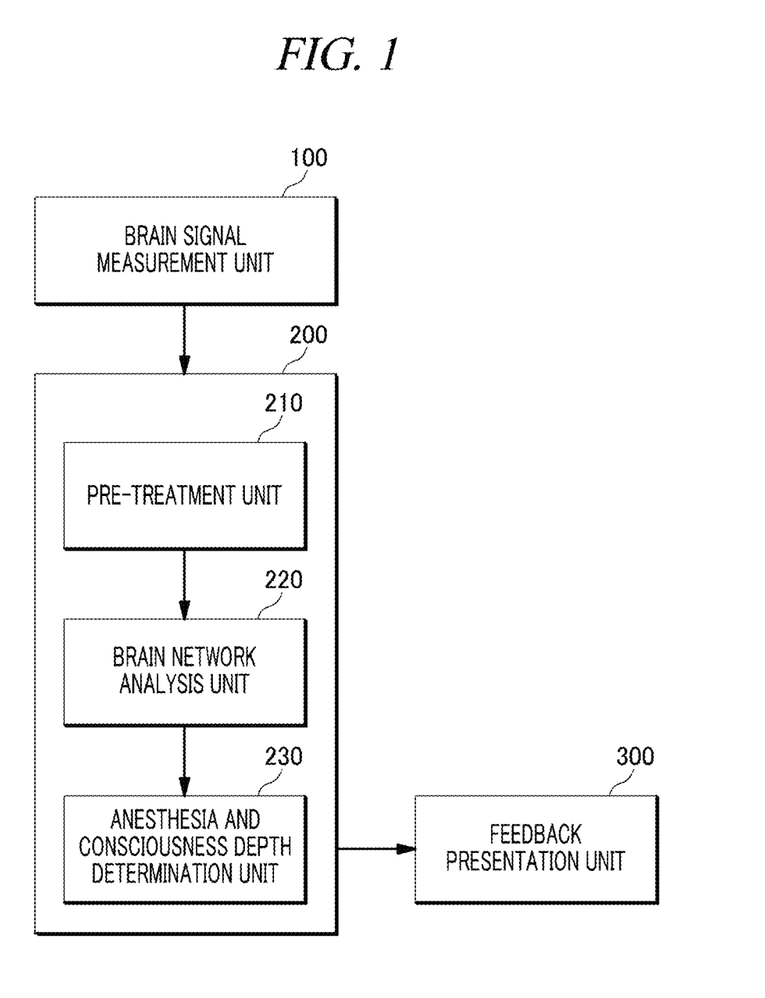
FIG. 1 is a configuration diagram showing an anesthesia and consciousness depth monitoring system using brain network analysis in accordance with various embodiments described herein.

FIG. 1 is a configuration diagram showing an anesthesia and consciousness depth monitoring system using brain network analysis in accordance with an embodiment of the present disclosure.

Referring to FIG. 1, a system according to an embodiment of the present disclosure includes a brain signal measurement unit 100, an anesthesia and consciousness depth monitoring apparatus 200, and a feedback presentation unit 300.

The brain signal measurement unit 100 measures electroencephalography (EEG) signals through multiple electrodes in contact with or adjacent to a user's scalp to measure an electrical signal changing depending on the user's anesthesia and consciousness depth. For example, the brain signal measurement unit 100 may measure brain signals from the occipital lobe for practical use. Herein, the user may be a patient under anesthesia. Particularly, when the patient is awake before the administration of an anesthetic, brain signals can be measured through the brain signal measurement unit 100. The anesthesia and consciousness depth monitoring apparatus 200 performs brain network analysis based on these measured brain signals, and a calculated brain network value can be used as reference data to determine the anesthesia and consciousness depth.

The anesthesia and consciousness depth monitoring apparatus 200 is connected wiredly or wirelessly to the brain signal measurement unit 100 to acquire the user's brain signals extracted during anesthesia, performs pre-treatment to the acquired brain signals to be suitable for brain network analysis, calculates a functional connectivity value between two channels for each frequency based on the pre-treated brain signals, and performs brain network analysis. Then, the anesthesia and consciousness depth monitoring apparatus 200 determines the anesthesia and consciousness depth of the user based on features of the analyzed brain network, and provides the determined anesthesia and consciousness depth of the user to the feedback presentation unit 300. Herein, the reference data obtained by analyzing the brain signals measured from patient in a waking state before the administration of the anesthetic may be comparted with data obtained by analyzing the brain signals of the patient measured from the patient under anesthesia after the administration of the anesthetic to determine the anesthesia and consciousness depth of the user. This method of determining the anesthesia and consciousness depth will be described in detail later with reference to FIG. 2.

The feedback presentation unit 300 visually presents the determined user's anesthesia and consciousness depth to the user through a user interface. For example, a quantitative index of the anesthesia and consciousness depth and an alarm to indicate the moment of transition between consciousness and unconsciousness may be provided. Details of the user interface will be described later with reference to FIG. 4.

Meanwhile, according to integrated Information theory, under consciousness, information integration is done in the cerebrum, whereas under unconsciousness, electroactive signals are generated but information integration is broken down. Recently, the occipital lobe has been referred to as the Posterior Hot Zone and found as a brain region having the strongest Neural correlates of consciousness and most clearly showing characteristics depending on the level of consciousness. That is, when a human body is put under anesthesia, consciousness transitions to unconsciousness and information integration capability of the nervous system is remarkably decreased and loss of consciousness occurs when spatial-temporal self-organization of brain waves is broken down. Particularly, when consciousness is lost, the amount of information flowing from the frontal lobe in charge of recognition to the occipital lobe in charge of sense is sharply decreased. Such a change in the brain between consciousness and unconsciousness cannot be explained only with simple indexes such as potential and frequency amplitude of brain waves.

Accordingly, the present disclosure suggests a method of quantifying interactions among brain nerves important for consciousness and unconsciousness to overcome the problems of the above-described technologies rather than simply analyzing electrical signals from brain. In other words, an anesthesia and consciousness depth can be measured accurately by understanding interactions between different regions through brain network analysis based on an integrated recognition paradigm suggesting that information integration of the brain-nervous system is changed by anesthesia. Further, consciousness depth can be measured using only interactions within the occipital lobe. To this end, brain signals form a patient are analyzed in real time and an anesthetic is administered to a user based on the functional connectivity of the user before anesthesia, and, thus, a changing functional connectivity can be measured.

Particularly, it is possible to provide the anesthesia and consciousness depth of the user by extracting functional connectivity indexes of brain signals during anesthesia and comparing them with a brain network state before anesthesia. Therefore, it is possible to provide the anesthesia and consciousness depth of the user as well as the moment of transition from consciousness and unconsciousness or the moment of transition from unconsciousness to consciousness. Accordingly, the present disclosure can be used as a bio-marker capable of accurately determining consciousness and unconsciousness.

Hereinafter, a configuration of the anesthesia and consciousness depth monitoring apparatus 200 using brain network analysis in accordance with an embodiment of the present disclosure will be described in detail.

Figure 2:
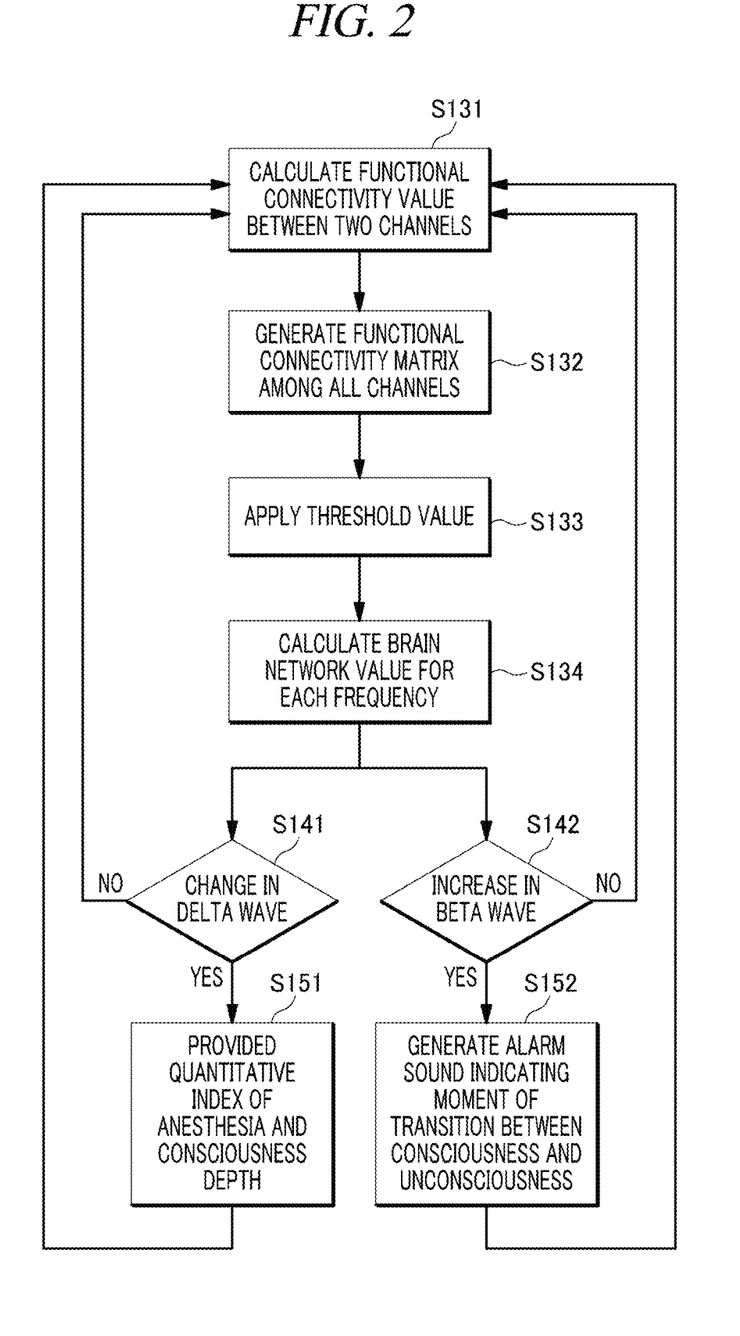
FIG. 2 is a flowchart provided to explain a method of performing brain network analysis by an anesthesia and consciousness depth monitoring apparatus in accordance with various embodiments described herein.

FIG. 2 is a flowchart provided to explain a method of performing brain network analysis by an anesthesia and consciousness depth monitoring apparatus in accordance with an embodiment of the present disclosure.

The anesthesia and consciousness depth monitoring apparatus 200 may include a memory configured to measure anesthesia and consciousness depth based on the level of consciousness using brain connectivity and a processor configured to execute the program (or application). Herein, the processor may perform various functions upon execution of the program stored in the memory, and may include a pre-treatment unit 210, a brain network analysis unit 220, an anesthesia and consciousness depth determination unit 230 as submodules for the respective functions.

The pre-treatment unit 210 receives a user's brain signals extracted during anesthesia from the brain signal measurement unit 100. The brain signals are electroencephalography (EEG) signals measured through multiple electrodes in contact with or adjacent to the user's scalp. Further, the pre-treatment unit 210 may remove noise caused by brain and eye movements or eye blink from the measured brain signals and perform filtering to the noise-removed brain signals in a specific frequency band related to sleep or consciousness.

Meanwhile, a delta ($\delta$) wave has a frequency of 0.1 to 4 Hz with an amplitude of 20 to 200 $\mu V$ and mainly occurs in a normal person during deep sleep or a newborn infant. A theta ($\theta$) wave has a frequency of 4 to 8 Hz with an amplitude of 20 to 100 $\mu V$ and occurs in an emotionally stable state or sleep state. An alpha ($\alpha$) wave has a frequency of 8 to 12 Hz with an amplitude of 20 to 60 $\mu V$ and occurs in a relaxed and comfortable state, and has a higher amplitude in a more stable state. A beta ($\beta$) wave has a frequency of 12 to 30 Hz with an amplitude of 2 to 20 $\mu V$ and occurs in a waking state or an active state of consciousness. A gamma ($\gamma$) wave has a frequency of 30 to 50 Hz with an amplitude of 2 to 20 $\mu V$ and occurs in a strongly excited state.

Therefore, the brain network analysis unit 220 of the present disclosure may use frequency bands of delta and beta waves that reflect consciousness and unconsciousness states.

Referring to FIG. 2, the brain network analysis unit 220 may extract frequency bands of delta and beta waves of the brain signals through frequency analysis. Then, the brain network analysis unit 220 may calculate a functional connectivity value between two channels based on the amplitude and phase values of the extracted frequency bands (S131). Then, the brain network analysis unit 220 may calculate functional connectivity values among all the channels for each frequency into a matrix (S132). Then, the brain network analysis unit 220 may apply a threshold value to determine whether or not the calculated functional connectivity values have significant connectivity (S133) and calculate a brain network value based on the graph theory (S134).

Herein, in the calculation of the functional connectivity value (S131), the functional connectivity value is a criterion to determine the degree of synchronization of phases between brain signals of the two channels and may include one or more of a phase locking value, a phase lag index, a weighted phase lag index, an imaginary coherence, and a synchronization likelihood.

Then, the brain network analysis unit 220 may convert the connectivity equal to or less than a specific threshold value into 0 to find out only the significant functional connectivity in the generation of the functional connectivity matrix (S132) and the application of the threshold value (S133). Herein, the threshold value may be set to a value with the greatest difference between a global efficiency and a local efficiency calculated from multiple random matrixes. For example, the threshold value may be set to a value with the greatest difference between a global efficiency and a local efficiency calculated from multiple (desirably, 1000 or more) random matrixes.

Then, a brain network value based on the graph theory is calculated from the functional connectivity matrix that represents only the significant connectivity in the calculation of the brain network value (S134) and compared with a waking state before anesthesia. The brain network value refers to a quantified value of the connectivity in the brain.

Specifically, brain network values are graph theory values known in the graph theory field. For example, the global efficiency is an integrated criterion of brain connectivity and represents the efficiency of information integration flow in the entire cerebrum, and the local efficiency is a separate criterion of brain connectivity and represents the network efficiency of information integration flow in a specific region of the cerebrum. Further, the brain network values are not limited thereto and may include at least one of graph theory values such as clustering coefficient, characteristic path length, modularity, closeness centrality, betweenness centrality, and eigenvector centrality that represent various features of brain connectivity.

Desirably, in the calculation of the brain network value (S134), one or more brain network values including the global efficiency and the local efficiency can be calculated.

The following Equation 1 represents the global efficiency.

$$E_{glob} = \frac{1}{N(N-1)} \sum_{i \neq j} \frac{1}{d_{ij}}$$ [Equation 1]

Herein, N represents the number of columns in a functional connectivity matrix, and $d_{ij}$ represents the shortest path between nodes 1 and j.

The following Equation 2 represents the local efficiency 2 and include Equation 1.

$$E_{loc} = \frac{1}{N} \sum_{i} E_{globc}(A_i)$$ [Equation 2]

Herein, N represents the number of columns in a functional connectivity matrix, and $A_i$ represents a subgraph between node i and its neighbors.

The anesthesia and consciousness depth determination unit 230 may detect the degree of increase in brain network value by comparing the brain network values with reference data in the delta wave and beta wave frequency bands as the time of anesthesia of the user passes. Herein, the reference data refer to brain network values analyzed form the user's brain signals measured from the user in a waking state before the administration of the anesthetic.

Referring to FIG. 2 again, for example, in the delta wave frequency band, a change (increase) in brain network value as compared with the reference data can be detected after the administration of the anesthetic (S141). That is, the increase in brain network value based on the reference data in the delta wave frequency band refers to a quantitative index that represents the anesthesia and consciousness depth. The change (increase) in brain network value in the delta wave frequency band will be described in detail later with reference to FIG. 3A and FIG. 3B.

Further, in the beta wave frequency band, the moment of increase in brain network value to a predetermined value or more as compared with the reference data can be detected after the administration of the anesthetic (S142). That is, the moment of increase in brain network value to a predetermined value or more as compared with the reference data in the beta wave frequency band refers to the moment of transition from consciousness and unconsciousness or the moment of transition from unconsciousness to consciousness. The increase (the moment of sharp increase) in brain network value in the beta wave frequency band will be described in detail later with reference to FIG. 3C and FIG. 3D.

Figure 3A:
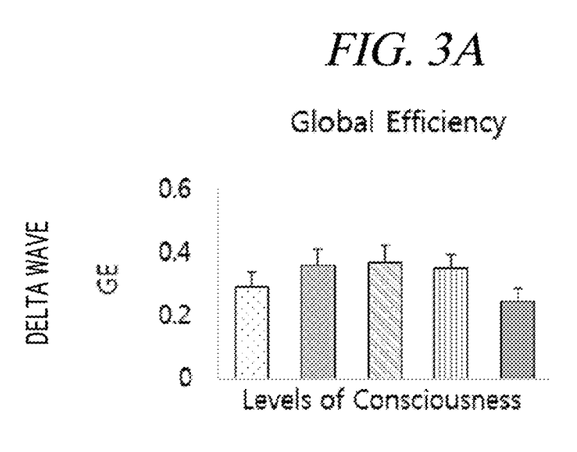
FIG. 3A shows values of global efficiency (GE) for respective anesthesia and consciousness depths in the delta frequency range of brain signals measured in accordance with various embodiments described herein.
Figure 3B:
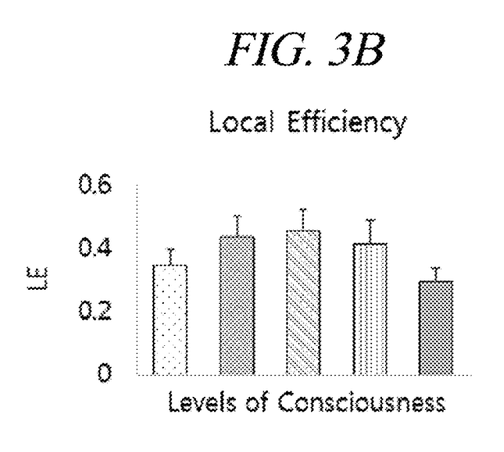
FIG. 3B shows values of local efficiency (LE) for respective anesthesia and consciousness depths in the delta frequency range.
Figure 3C:
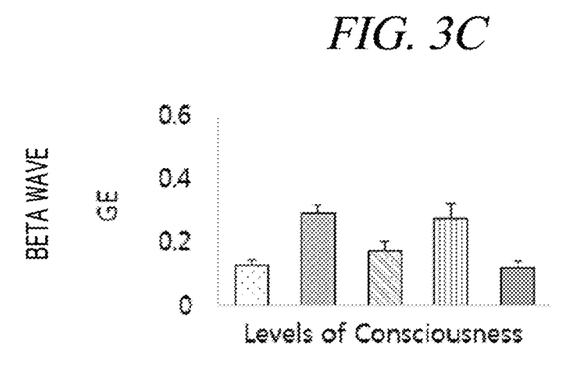
FIG. 3C shows values of global efficiency (GE) for respective anesthesia and consciousness depths in the beta frequency range.
Figure 3D:
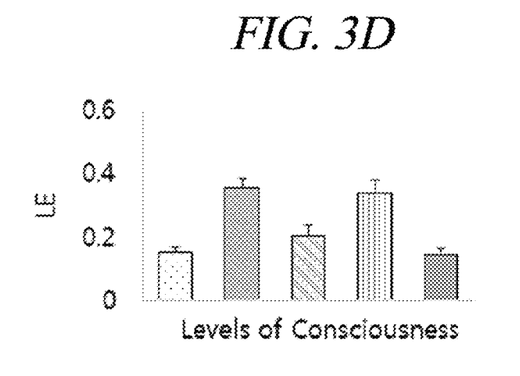
FIG. 3D shows values of local efficiency (LE) for respective anesthesia and consciousness depths in the beta frequency range.

FIG. 3A shows values of global efficiency (GE) for respective anesthesia and consciousness depths in the delta frequency range of brain signals measured in accordance with an embodiment of the present disclosure, FIG. 3B shows values of local efficiency (LE) for respective anesthesia and consciousness depths in the delta frequency range, FIG. 3C shows values of global efficiency (GE) for respective anesthesia and consciousness depths in the beta frequency range, and FIG. 3D shows values of local efficiency (LE) for respective anesthesia and consciousness depths in the beta frequency range.

Referring to FIG. 3A to FIG. 3D, 1 marked on each bar graph represents a standard deviation. Particularly, the anesthesia and consciousness depth can be classified into 5 stages: a waking state before the administration of an anesthetic (Baseline); the moment of transition from consciousness and unconsciousness after the administration of an anesthetic (TransUN); a unconscious state in which there is no response to any stimulus due to the administration of the anesthetic (UCS), the moment of transition from unconsciousness to consciousness (TransCON); and a recovery and conscious state in which there may be a response to a stimulus (Recovery). Herein, a network value in the waking state before the administration of an anesthetic (Baseline) is used as reference data to compare the degree of increase in network value during anesthesia.

In other words, as illustrated in FIG. 3A and FIG. 3B, the delta wave shows an increase of brain network values (GE and LE) in the other stages except the recovery state (Recovery) as compared with the waking state (Baseline). That is, the delta wave shows that as the brain network values (GE and LE) increase, the anesthesia and consciousness depth increases.

As illustrated in FIG. 3C and FIG. 3D, the beta wave shows an increase of brain network values (GE and LE) only at the moment of transition from consciousness and unconsciousness (TransUN) or the moment of transition from unconsciousness to consciousness (TransCON) as compared with the waking state (Baseline). That is, the beta wave shows that the moment of sharp increase in brain network values (GE and LE) to predetermined values or more as compared with the waking state (Baseline) refers to the moment of transition from consciousness and unconsciousness or the moment of transition from unconsciousness to consciousness.

Figure 4:
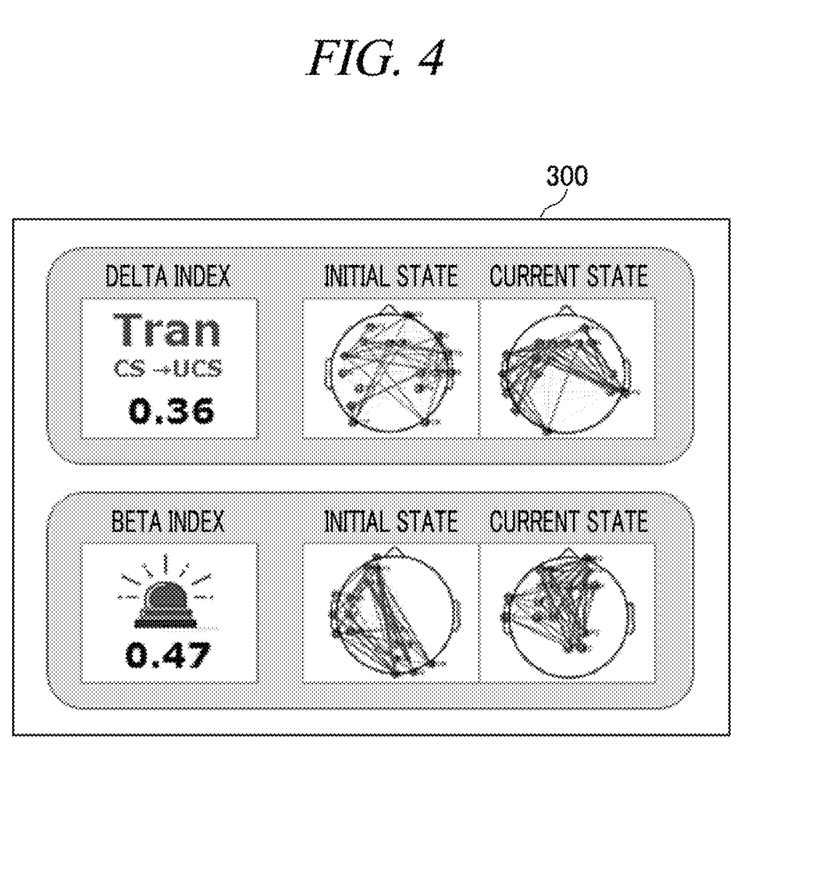
FIG. 4 is an example diagram of a user interface that displays a user's anesthesia and consciousness depth determined by an anesthesia and consciousness depth monitoring apparatus through brain network analysis in accordance with various embodiments described herein.

FIG. 4 is an example diagram of a user interface that displays a user's anesthesia and consciousness depth determined by an anesthesia and consciousness depth monitoring apparatus through brain network analysis in accordance with an embodiment of the present disclosure.

As illustrated in FIG. 4, the feedback presentation unit 300 visually presents the brain network values of the delta wave indicating the anesthesia and consciousness depth as an quantitative index and provides the brain network values of the beta wave as an alarm indicating the moment of transition between consciousness and unconsciousness.

Specifically, referring to FIG. 2 again, the network value which is increased compared with the reference data in the delta wave frequency band may be provided as a quantitative index of the anesthesia and consciousness depth through the feedback presentation unit 300 (S151). Further, the moment of increase in brain network value to a predetermined value or more in the beta wave frequency band may be detected and then provided as an alarm to indicate the moment of transition between consciousness and unconsciousness through the feedback presentation unit 300 (S152).

As illustrated in FIG. 4, the alarm may be provided as an alarm sound to be auditorily recognized or as a warning light to be visually recognized. For example, the feedback presentation unit 300 may display a brain network value (delta index, beta index) in the delta wave or beta wave frequency band as a quantitative index of the anesthesia and consciousness depth. For another example, a functional connectivity pattern of an initial state (waking state) and a current state (unconscious state under anesthesia) in the delta wave or beta wave frequency band may be displayed.

Therefore, the anesthesia and consciousness depth monitoring system using brain network analysis according to the present disclosure can objectively predict an anesthesia and consciousness depth and accurately find out the moment of transition between consciousness and unconsciousness and thus can be actually used in clinic practice such as additional administration of an anesthetic.

Further, the depth of a user's consciousness is provided by measuring an anesthesia and consciousness depth using the above-described brain network values and the moment of transition from consciousness and unconsciousness or the moment of transition from unconsciousness to consciousness is found and provided as an alarm. Thus, it is possible to prevent accidents such as anesthesia awareness which can happen during surgery. Furthermore, a waking state of the user before anesthesia becomes a criterion, and, thus, an anesthesia and consciousness depth can be corrected by checking variables such as the user's conditions on the day of surgery.

Figure 5:
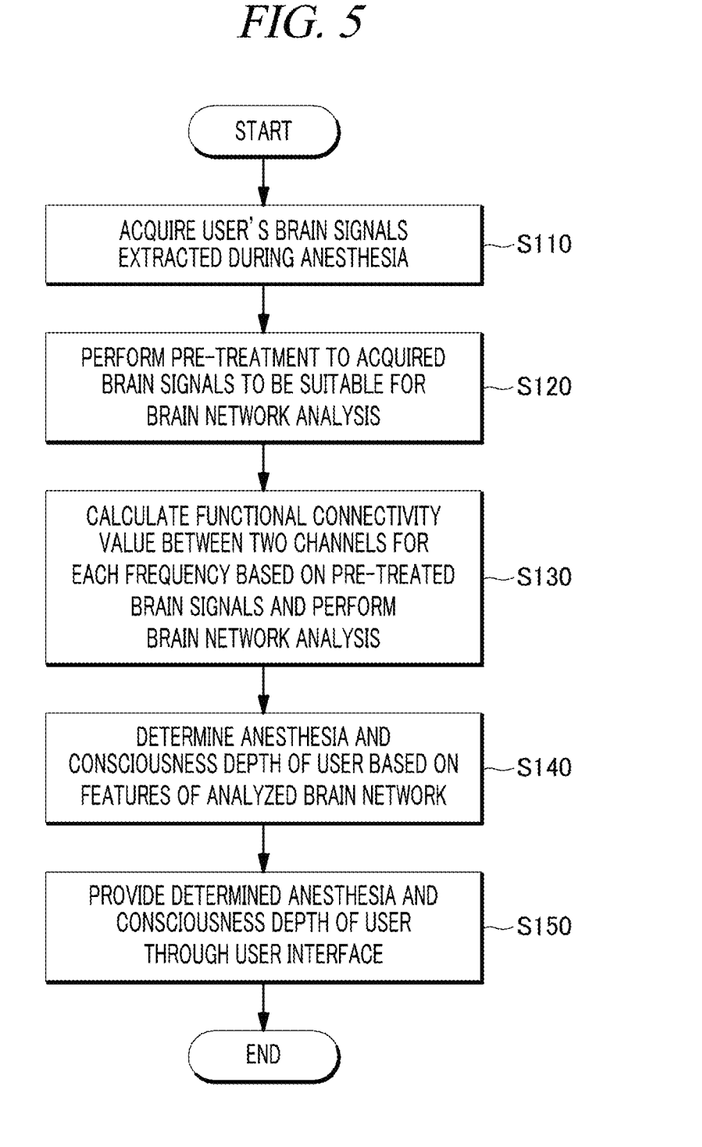
FIG. 5 is a flowchart provided to explain a method of monitoring an anesthesia and consciousness depth through brain network analysis in accordance with various embodiments described herein.

FIG. 5 is a flowchart provided to explain a method of monitoring an anesthesia and consciousness depth through brain network analysis in accordance with an embodiment of the present disclosure.

Hereinafter, the method of monitoring an anesthesia and consciousness depth through brain network analysis according to an embodiment of the present disclosure will be described in detail with reference to FIG. 5.

The following method is performed by the above-described apparatus 200. Therefore, the above descriptions may be applied to the following method, even though they are omitted hereinafter.

The method of monitoring an anesthesia and consciousness depth through brain network analysis by a computing device includes: acquiring a user's brain signals extracted during anesthesia (S110); performing pre-treatment to the acquired brain signals to be suitable for brain network analysis (S120); calculating a functional connectivity value between two channels for each frequency based on the pre-treated brain signals and performing brain network analysis (S130); determining an anesthesia and consciousness depth of the user based on features of the analyzed brain network (S140); and providing the determined anesthesia and consciousness depth of the user through a user interface (S150).

The performing of the pre-treatment (S120) includes removing noise from the acquired brain signals and filtering the noise-removed brain signals in a specific frequency band related to sleep or consciousness.

The performing of the brain network analysis (S130) includes extracting frequency bands of delta and beta waves of the brain signals through frequency analysis, calculating a functional connectivity value between two channels based on the amplitude and phase values of the extracted frequency bands, and applying a threshold value to determine whether or not the calculated functional connectivity value has significant connectivity and calculating a brain network value based on the graph theory.

Herein, the functional connectivity value is a criterion to determine the degree of synchronization of phases between brain signals of the two channels and includes one or more of a phase locking value, a phase lag index, a weighted phase lag index, an imaginary coherence, and a synchronization likelihood.

Further, the threshold value is set to a value with the greatest difference between a global efficiency and a local efficiency calculated from multiple random matrixes, and the brain network value refers to a quantified value of the connectivity in the brain.

The determining of the anesthesia and consciousness depth of the user (S140) includes detecting the degree of increase in brain network value by comparing brain network values with reference data in the delta wave and beta wave frequency bands as the time of anesthesia of the user passes. Herein, the increase in brain network value based on the reference data in the delta wave frequency band refers to a quantitative index that represents the anesthesia and consciousness depth, and the moment of increase in brain network value to a predetermined value or more as compared with the reference data in the beta wave frequency band refers to the moment of transition from consciousness and unconsciousness or the moment of transition from unconsciousness to consciousness. Herein, the reference data refer to brain network values analyzed form the user's brain signals measured from the user in a waking state before the administration of the anesthetic.

The embodiments of the present disclosure can be embodied in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage. The computer storage medium includes all volatile/non-volatile and removable/non-removable media embodied by a certain method or technology for storing information such as computer-readable instruction code, a data structure, a program module or other data. The method and system of the present disclosure have been explained in relation to a specific embodiment, but their components or a part or all of their operations can be embodied by using a computer system having general-purpose hardware architecture.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF REFERENCE NUMERALS

100: Brain signal measurement unit
200: Anesthesia and consciousness depth monitoring apparatus
210: Pre-treatment unit
220: Brain network analysis unit
230: Anesthesia and consciousness depth determination unit
300: Feedback presentation unit

We claim:

1. A method of monitoring an anesthesia and consciousness depth through brain network analysis by a computing device, comprising:
    acquiring a user's brain signals extracted during anesthesia;
    performing pre-treatment to the acquired brain signals to be suitable for brain network analysis;
    calculating a functional connectivity value between two channels for each frequency based on the pre-treated brain signals and performing brain network analysis;
    determining an anesthesia and consciousness depth of the user based on the functional connectivity value and the brain network analysis; and
    providing the anesthesia and consciousness depth of the user through a user interface, wherein the calculating of the functional connectivity value includes: extracting frequency bands of delta and beta waves of the brain signals through frequency analysis;
    calculating the functional connectivity value between the two channels based on amplitudes and phase values of the extracted frequency bands; and
    applying a threshold value to determine whether or not the calculated functional connectivity value has significant connectivity and calculating a brain network value based on a graph theory, wherein the threshold value is set to a value with the greatest difference between a global efficiency and a local efficiency calculated from multiple random matrixes.

2. The method of monitoring an anesthesia and consciousness depth through brain network analysis of claim 1, wherein the performing of the pre-treatment to the acquired brain signals to be suitable for brain network analysis includes:
    removing noise from the acquired brain signals; and
    filtering the noise-removed brain signals in a specific frequency band related to sleep or consciousness.

3. The method of monitoring an anesthesia and consciousness depth through brain network analysis of claim 1, wherein the functional connectivity value is a criterion to determine a degree of synchronization of phases between brain signals of the two channels and includes one or more of a phase locking value, a phase lag index, a weighted phase lag index, an imaginary coherence, and a synchronization likelihood, and
    wherein the brain network value refers to a quantified value of the connectivity in the brain.

4. The method of monitoring an anesthesia and consciousness depth through brain network analysis of claim 1, wherein the determining of the anesthesia and consciousness depth of the user based on features of the analyzed brain network includes:
    detecting a degree of increase in the brain network value by comparing brain network values with reference data in the delta wave and beta wave frequency bands as a time of anesthesia of the user passes,
    wherein the increase in brain network value based on the reference data in the delta wave frequency band refers to a quantitative index that represents the anesthesia and consciousness depth,
    wherein a moment of increase in the brain network value to a predetermined value or more as compared with the reference data in the beta wave frequency band refers to a moment of transition from consciousness and unconsciousness or a moment of transition from unconsciousness to consciousness, and
    wherein the reference data refer to brain network values analyzed form the user's brain signals measured from the user in a waking state before an administration of an anesthetic.

5. An apparatus of monitoring an anesthesia and consciousness depth through brain network analysis, comprising:
    a memory in which a program configured to perform a method of monitoring an anesthesia and consciousness depth through brain network analysis is stored; and
    a processor that executes the program,
    wherein upon execution of the program, the processor acquires a user's brain signals extracted during anesthesia,
    performs pre-treatment to the acquired brain signals to be suitable for brain network analysis, calculates a functional connectivity value between two channels for each frequency based on the pre-treated brain signals and performs the brain network analysis, determines an anesthesia and consciousness depth of the user based on the functional connectivity value and the brain network analysis;, and provides the determined anesthesia and consciousness depth of the user through a user interface, wherein the processor extracts frequency bands of delta and beta waves of the brain signals through frequency analysis, calculates the functional connectivity value between the two channels based on amplitudes and phase values of the extracted frequency bands, and applies a threshold value to determine whether or not the calculated functional connectivity value has significant connectivity and calculates a brain network value based on a graph theory, and wherein the threshold value is set to a value with the greatest difference between a global efficiency and a local efficiency calculated from multiple random matrixes.

6. The apparatus of monitoring an anesthesia and consciousness depth through brain network analysis of claim 5, wherein the processor removes noise from the acquired brain signals and performs filtering to the noise-removed brain signals in a specific frequency band related to sleep or consciousness.

7. The apparatus of monitoring an anesthesia and consciousness depth through brain network analysis of claim 5, wherein the functional connectivity value is a criterion to determine the degree of synchronization of phases between brain signals of the two channels and includes one or more of a phase locking value, a phase lag index, a weighted phase lag index, an imaginary coherence, and a synchronization likelihood, and wherein the brain network value refers to a quantified value of the connectivity in the brain.

8. The apparatus of monitoring an anesthesia and consciousness depth through brain network analysis of claim 5, wherein the processor detects a degree of increase in the brain network value by comparing brain network values with reference data in the delta wave and beta wave frequency bands as a time of anesthesia of the user passes, wherein the increase in brain network value based on the reference data in the delta wave frequency band refers to a quantitative index that represents the anesthesia and consciousness depth, wherein a moment of increase in the brain network value to a predetermined value or more as compared with the reference data in the beta wave frequency band refers to a moment of transition from consciousness and unconsciousness or a moment of transition from unconsciousness to consciousness, and wherein the reference data refer to brain network values analyzed form the user's brain signals measured from the user in a waking state before an administration of an anesthetic.

* * * * *